United States Patent [19]
Schwartz

[11] 3,961,419
[45] June 8, 1976

[54] METHOD OF CUTTING AND REMOVING SUTURES

[76] Inventor: Boris Schwartz, 400 Park Ave., Paterson, N.J. 07504

[22] Filed: June 30, 1975

[21] Appl. No.: 592,087

[52] U.S. Cl. .............................. 128/303 R; 30/34.2; 30/124; 128/334 R
[51] Int. Cl.² .................. A61B 17/10; A61B 17/32; A61B 19/00
[58] Field of Search ........ 128/303 R, 334 R, 334 C; 30/34.2, 124

[56] References Cited
UNITED STATES PATENTS

| | | | |
|---|---|---|---|
| 2,696,621 | 12/1954 | Miller | 30/124 X |
| 3,624,683 | 11/1971 | Matles | 30/124 |
| 3,879,846 | 4/1975 | Allen | 30/124 |

FOREIGN PATENTS OR APPLICATIONS

| | | | |
|---|---|---|---|
| 1,172,307 | 11/1969 | United Kingdom | 128/334 R |

OTHER PUBLICATIONS
"Easy Removal of Skin Sutures," by Weinstein et al., J.A.M.A., vol. 152, No. 13, July 25, 1953.

Primary Examiner—Al Lawrence Smith
Assistant Examiner—J. T. Zatarga
Attorney, Agent, or Firm—Ralph R. Roberts

[57] ABSTRACT

An inexpensive suture cutter is shown in which the cutting portion is a sharpened edge of a wire-like member one-eighth inch or less in diameter at the cutting portion. This wire-like cutting portion has a blunt end to prevent accidental penetration of the skin as the knife portion of the cutter is slid under the sutures which are then cut as the cutting edge is slid along and underneath the sutures. Prior to cutting a length of adhesive tape is placed on and secured to the sutures to be cut and removed. The edge of the tape is placed adjacent or over the proposed cutting path. The sutures are removed by and when the tape is lifted from the skin after the sutures have been severed by the cutter.

5 Claims, 5 Drawing Figures

METHOD OF CUTTING AND REMOVING SUTURES

BACKGROUND OF THE INVENTION

1. Field of the Invention

With reference to the classification of art as established in the United States Patent Office the present invention is found in the general Class entitled, "Surgery" (Class 128) and in the subclass entitled, "tweezers" (subclass 354). Applicable art is also found in the Class entitled, "Cutlery" (Class 30) and in the subclass thereunder entitled, "razors-combined with means to lift hair or skin" (subclass 34.2).

2. Description of the Prior Art

The removal of stitches from incisions is generally performed by a doctor and/or medical assistant. The sutures are generally cut and removed by the use of special sissors and forceps or tweezers by which the cut suture may be grasped and pulled from the healed incision. The present invention has for this purpose an apparatus and method which provides an inexpensive improvement for the cutting and removal of sutures. The present invention contemplates an inexpensive cutter constructed of wire with an end of the wire curved and formed to provide a finger gripping and manipulative portion. This wire-like suture cutting device is made of low carbon steel. This cutter is used with a given length of adhesive gauze or the like. The suture cutter and the gauze are both inexpensive and it is proposed and contemplated that these will be discarded after use. This wire-like cutter, although it has a sharp edge sufficient for cutting several sutures, is not contemplated to have a sustaining sharp edge as the cutter will be discarded after this one use.

An attempt to provide a combination suture cutter and remover is found in U.S. Pat. No. 3,879,846 as issued on Apr. 29, 1975 to ALLEN, JR. which provides a combination implement for cutting and removing surgical sutures consisting of a portion forming a forceps and a longitudinal suture cutting element extending between the arms of the forceps and anchored to one arm and the bight of the forceps body. This device requires a tweezer grasping action to lift and pull the suture. The very low profile cutting blade of this application with its immediate severing action is not shown in this or other known prior art. The sliding cut employed by this cutter minimizes the effort to cut the sutures and the tape used to lift and remove the cut sutures is easily manipulated.

SUMMARY OF THE INVENTION

This invention may be summarized at least in part with reference to its objects.

It is an object of this invention to provide a method of suture removal which is not only inexpensive and can be performed without assistance by the surgeon but is also very rapid. This method is quite convenient for both the patient and for the one removing the sutures. It is contemplated that the suture cutter be made of small diameter wire and have a short portion formed with a small cutting edge and a blunt entering end. This cutting portion in use is slid underneath the suture and as the sharp edge is slid along a path transverse to the suture the suture is cut. To assist in removing the sutures which customarily are pulled from the skin by tweezers, forceps and the like it is contemplated that a length of adhesive tape or adhesive coated material be placed upon the uncut sutures prior to their being cut. As the suture is severed the tape is lifted from the skin and with the severed suture adhered to the tape is pulled from the skin. After the tape and the attached sutures are removed from the skin of the patient the tape and the cutter are discarded.

The suture cutter, to be hereinafter more fully described, resembles a large paper clip with one of the legs of the clip partially pulled from the original configuration, this leg portion is formed with a knife-like edge.

It is a further object of this invention to provide, and it does provide, an inexpensive suture cutter and removal apparatus which is contemplated to have a one time use. A cutter made of wire of one-eighth inch diameter or less may be shaped much like a common large paper clip. One of the legs of this wire form is formed with a sharp edge and the end is blunt to prevent skin penetration at the time of suture cutting. With this cutter is provided a length of adhesive tape which is pressed onto the skin and sutures before cutting. One end of the tape is then lifted sufficiently for the entrance of the cutting portion of the cutter which is slid under the suture and then advanced to cut the suture. As the cutter is advanced the tape is lifted to enable the sutures to be sequentially cut until all are cut after which the tape and adhered sutures are removed and discarded.

In addition to the above summary the following disclosure is detailed to insure adequacy and aid in understanding of the invention. This disclosure, however, is not intended to cover each variation in form or additions of further improvements. For this reason there has been chosen a specific embodiment of the cutter and adhesive tape strip as adopted for use in removing cut sutures and showing a preferred means for apparatus and method. This specific embodiment has been chosen for the purpose of illustration and description as shown in the accompanying drawing wherein:

Figure 1:
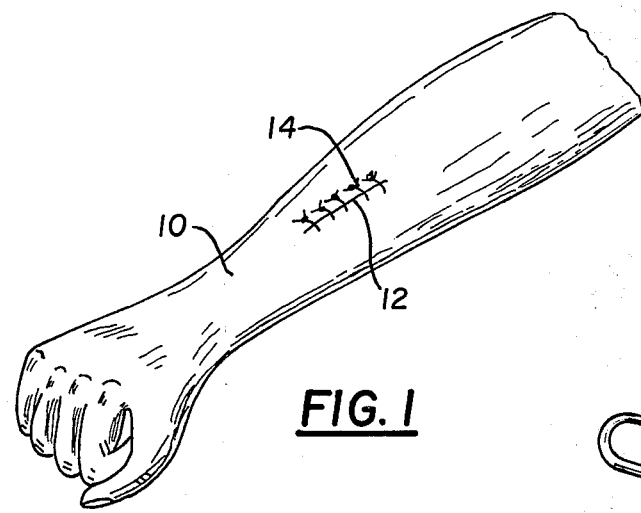
FIG. 1 represents an arm of the patient and showing sutures as used to close a cut.
Figure 3:
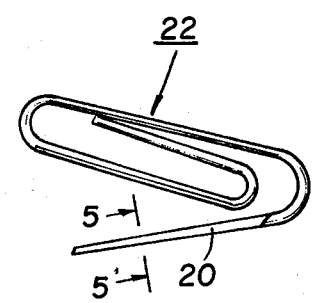
FIG. 3 represents a side view of a suture cutter in substantially a full size.

In the following description and in the claims the details are identified by specific names for convenience; these names, however, are intended to be generic in their application. Corresponding reference characters refer to like members throughout the figures of the drawing. The drawing and specification disclose pertinent details but it should be understood that structural details may be modified and that the suture cutter may be incorporated in other structural forms than shown.

DESCRIPTION OF THE SUTURE CUTTER AND METHOD OF REMOVING CUT SUTURES

Figure 2:
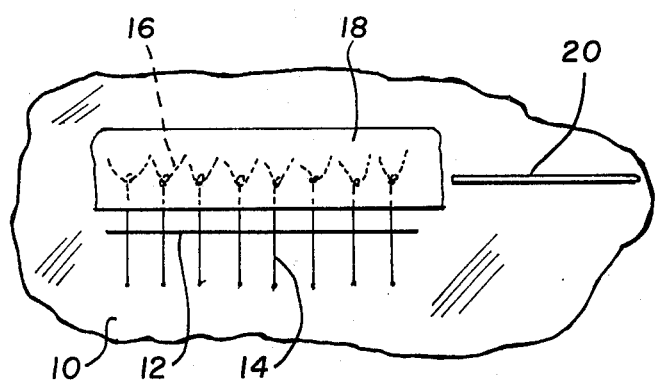
FIG. 2 represents an enlarged view of a cut closed with a series of spaced sutures and an adhesively coated tape placed over a portion of the sutures and indicating a proposed path of the cutting blade portion of the suture cutter prior to the cutting of the sutures.

Referring now in particular to the drawing, there is shown a typical representation of the suturing of a cut on an arm 10 of a patient having a cut 12 closed for healing by a plurality of sutures 14. These sutures are inserted and tied in the normal manner and as is customary the positioning and spacing are neatly arranged. In FIG. 2 is shown in an enlarged view the typical arm 10 having a cut 12 closed by a plurality of sutures 14. It is anticipated that the knotted portions of the sutures, which are indicated as 16, may lay more-or-less in a straight line in which case an adhesive tape 18 is placed over these suture knots to tightly adhere the knots and adjacent suture portions to the adhesive side of the tape. Preferably this tape has an adhesive coating as is adapted for ready disengagement from skin. This is the adhesive preferable for use with the tape 18. With the placement of the adhesively surfaced tape on the sutures the knife cutting portion 20 of the suture cutter, generally indicated as 22, is brought to the sutured area.

Use of Suture Cutter and Method of Removing Cut Sutures

Figure 4:
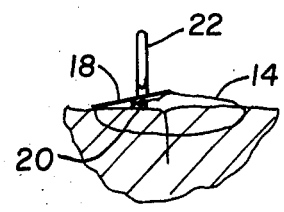
FIG. 4 represents in an enlarged scale a sectional view showing the placement of the cutting edge of the suture cutter in relation to a typical suture and of the tape used to achieve a lifting and removal of the cut suture.
Figure 5:
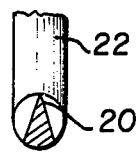
FIG. 5 represents an enlarged view taken on the line 5—5 of FIG. 3 and showing the construction of the cutting portion of the suture cutter.

To use the apparatus of this invention the surgeon or attendant lifts one end portion of the affixed tape 18 sufficiently for the blunt end and cutting portion 20 to be brought to and under the suture as in FIG. 4. The knife portion is then advanced with a slight upward urging of the blade so as to slice the suture, as the cutting edge portion is advanced forward. In the meantime, the tape is lifted sufficiently for the cutting portion to slide under the next suture. As progressively the sutures are cut, the tape at these cut sutures is lifted. This method enables all the sutures to be cut in a sequential manner. After all the sutures are cut the adhered cut sutures and tape are pulled from the skin and the now removed sutures and tape are discarded. If these are the only sutures to be removed at this time it is contemplated that the suture cutter will also be discarded.

It is to be noted that the suture cutter is made of a relatively low carbon steel wire and as a knife has no other use or dangerous potential. The cost of such a suture cutter made in large quantities can be produced for one or two cents or less if the cutting edge portion 20 is made by an automatic swaging or shaping action. Since this is a one time use of a product, after the shaping of the edge the suture cutter as a whole may be lightly washed-plated or lightly coated prior to its being sealed in a package for storage and shipment. The cost of such treating of the steel member is only a few cents per thousand.

The method of this invention includes the placing of an adhesively coated tape-like member over a series of sutures with the exposed suture portions embedded in the adhesive portion of the tape. The tape is progressively lifted as the sutures are cut. Cutting of the sutures is achieved by a forward slicing action. A cutting portion is formed on a steel wire of less than one-eighth of an inch in diameter. As reduced to practice, the preferred wire diameter of one-sixteenth of an inch is formed with a sharpened edge and a blunt forward end. A portion of the wire is formed into a loop-like configuration to provide a small manipulative handle. As a method the steps of removing the sutures include the placing of an adhesively coated tape over a series of sutures; partially lifting the tape to permit the passage underneath the tape and below the suture of a very small light cutting blade of less than one-eighth of an inch in height. said blade being a substantially straight member which is slid along the skin and as it is advanced a slight upward force is applied against the uncut suture which is severed with a forward slicing action. The cutting edge is advanced under the next adjacent suture while at the same time the tape is lifted sufficiently for the entrance and passage of the cutting edge of the knife under the lifted tape and the uncut sutures. As the sutures are successively cut an eventual cutting and removing of all of the sutures is achieved. The embedded sutures are sufficiently attached to the adhesively coated tape so that as the tape is pulled from the surface of the skin the embedded and severed sutures are removed from the healed cut.

Terms such as "left", "right", "up", "down", "bottom", "top", "front", "back", "in", "out" and the like are applicable to the suture cutter and tape as shown and described in conjunction with the drawing. These terms are merely for the purposes of description and do not necessarily apply to the position in which the cutter and tape may be placed on the patient or may be constructed or used.

While a particular embodiment of the cutter and tape and the method of suture removal provided thereby have been shown and described it is to be understood modifications may be made within the scope of the accompanying claims and protection is sought to the extent the prior art allows.

What is claimed is:

1. The method of cutting and removing surgical sutures with apparatus having a potential one time use, said method including the steps of: (a) forming a cutting blade member having a height not exceeding one-eighth inch, this cutting blade member being made of inexpensive metal and having a blunt end formed on the distal end of this member and adjacent thereto is formed a cutting blade portion, this blunt end being configured so as to make accidental penetration of the skin difficult; (b) forming the cutting blade portion with an edge of a sufficient sharpness so as to sever surgical sutures when this cutting edge portion is brought underneath the suture and while in tensioned engagement with the suture moving the cutting edge so as to slide the cutting edge across the suture and with a slight upward pressure effect a cutting of the suture; (c) forming a handle means and attaching it to the cutting blade portion to provide a cutter assembly to enable grasping and manipulating of this cutter assembly so as to guide and slide the cutting blade portion under and across the sutures, and (d) supplying a length of flexible tape-like material having one surface coated with an adhesive having sufficient adhesion to entrap and retain the sutures and pulling the sutures from the skin of the patient as the sutures are cut and pressing this length of tape onto the uncut sutures prior to their being severed by the cutter.

2. The method of cutting and removing surgical sutures as in claim 1 which further includes forming the suture cutter of steel wire which is less than three-thirty-seconds of an inch in diameter.

3. The method of cutting and removing surgical sutures as in claim 2 in which the forming of the handle includes the step of bending a connected portion of wire out of the plane of the cutting portion.

4. The method of cutting and removing surgical sutures as in claim 3 which includes the step of forming the cutting edge as by swaging.

5. The method of cutting and removing surgical sutures as in claim 3 which further includes the step of protecting the cutter against rust and the like by providing at least a light plating.

* * * * *